United States Patent
Vepa et al.

(10) Patent No.: US 9,480,432 B2
(45) Date of Patent: Nov. 1, 2016

(54) PROCESSING OF PERIODIC PHYSIOLOGICAL SIGNALS

(75) Inventors: Jithendra Vepa, Eindhoven (NL); Nagaraju Bussa, Eindhoven (NL); Srinivas Rao Kudavelly, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 13/877,289

(22) PCT Filed: Sep. 26, 2011

(86) PCT No.: PCT/IB2011/054216
§ 371 (c)(1),
(2), (4) Date: Apr. 1, 2013

(87) PCT Pub. No.: WO2012/046158
PCT Pub. Date: Apr. 12, 2012

(65) Prior Publication Data
US 2013/0197379 A1    Aug. 1, 2013

(30) Foreign Application Priority Data
Oct. 8, 2010    (EP) .................................... 10186933

(51) Int. Cl.
| | | |
|---|---|---|
| *A61B 5/0452* | (2006.01) | |
| *A61B 5/00* | (2006.01) | |
| *A61B 5/0245* | (2006.01) | |
| *A61B 5/0402* | (2006.01) | |
| *A61B 7/00* | (2006.01) | |
| *A61B 5/04* | (2006.01) | |

(52) U.S. Cl.
CPC ........... *A61B 5/7203* (2013.01); *A61B 5/0245* (2013.01); *A61B 5/0402* (2013.01); *A61B 5/04012* (2013.01); *A61B 5/742* (2013.01); *A61B 5/7405* (2013.01); *A61B 5/7455* (2013.01); *A61B 7/00* (2013.01); *A61B 5/04* (2013.01); *A61B 5/0452* (2013.01); *A61B 5/7232* (2013.01)

(58) Field of Classification Search
CPC A61B 5/0452; A61B 5/7203; A61B 5/0402; A61B 5/0456; A61B 5/9203; A61B 5/0245; A61B 5/04012; A61B 5/7405; A61B 5/742; A61B 5/7455; A61B 5/7232
USPC ................................ 600/513–517, 521, 528
See application file for complete search history.

(56) References Cited

U.S. PATENT DOCUMENTS

| | | | |
|---|---|---|---|
| 4,446,873 | A | 5/1984 | Groch et al. |
| 5,628,326 | A | 5/1997 | Arand et al. |

(Continued)

FOREIGN PATENT DOCUMENTS

| | | |
|---|---|---|
| JP | 2003325464 A | 11/2003 |
| WO | 9427492 A1 | 12/1994 |

(Continued)

*Primary Examiner* — Michael Kahelin
*Assistant Examiner* — Minh Duc Pham (57) ABSTRACT

Signal processing devices normally filter the signal to reduce noise. Any filtering is likely to eliminate useful components of the signal too. A device for and method of signal processing is disclosed, wherein intrinsically clean signal cycles are selected for reproduction so that the processed signal retains components of all frequencies. A system that uses the disclosed device and the method for processing periodic physiological signals is also disclosed.

19 Claims, 4 Drawing Sheets

(56) References Cited

U.S. PATENT DOCUMENTS

| | | |
|---|---|---|
| 6,217,525 B1 | 4/2001 | Medema et al. |
| 2004/0176696 A1* | 9/2004 | Mortara ............... A61B 5/0452 600/515 |
| 2008/0171945 A1* | 7/2008 | Dotter .................... A61B 5/024 600/514 |
| 2009/0228057 A1 | 9/2009 | Allavatam et al. |
| 2009/0281441 A1* | 11/2009 | Zhang .................. A61B 5/0468 600/516 |
| 2011/0230776 A1* | 9/2011 | Milpied ............. A61B 5/04011 600/516 |

FOREIGN PATENT DOCUMENTS

| | | |
|---|---|---|
| WO | 9717015 A1 | 5/1997 |
| WO | 2009138932 A1 | 11/2009 |
| WO | 2010054863 A1 | 5/2010 |

\* cited by examiner

PROCESSING OF PERIODIC PHYSIOLOGICAL SIGNALS

FIELD OF THE INVENTION

The following belongs to the field of signal processing. It belongs to the field of processing of physiological signals and in particular periodic physiological signals.

BACKGROUND OF THE INVENTION

A General Medical Practitioner (GP) auscultates using a stethoscope to listen to heart sounds for finding abnormalities, if any, in the patient's heart. To make a reliable diagnosis a GP needs to be skilled and needs a good stethoscope. An independent study (IEEE TBME, 2007) indicated that about eighty percent of the patients referred by GPs to specialists after evaluation using stethoscopes are found to be normal. This shows that it is difficult to make accurate diagnosis using a stethoscope.

Digital stethoscopes are available in the market today. They reduce ambient noise heard by the user by filtering, enhance the heart sounds, store the sounds and some also display a visual representation of them.

SUMMARY OF THE INVENTION

Such devices normally filter the signal to reduce noise. Any filtering is likely to eliminate useful components of the signal too.

It is preferable to have a signal processing device that provides a signal that retains all the frequency components of the original signal and still the signal has less noise, for instance, than the original signal.

Such a signal processing device for processing a periodic physiological signal from a subject is disclosed, the device comprising a cycle detection unit for detecting a cycle of the signal, an analysis unit for determining a value of a characteristic of the cycle, a selection unit for discarding or storing the cycle based on the determined value and a concatenating unit for concatenating the stored cycle for generating a concatenated signal for outputting for a user.

Such a device provides selected cycles of periodic physiological signals. The signal contains all the frequency components of the original signal and may still be less noisy and hence more useful to a user. The device may also have the additional advantage of having low energy consumption since selection of single cycles of signals is less computation intensive and consequently less energy intensive.

The disclosed device may be used for processing a signal representative of the heartbeats of a subject. The signal representative of the heartbeats may be the sounds produced by a beating heart or the Electrocardiogram (ECG) signal of a subject, for example.

It is also preferable to have a method of processing periodic physiological signals from a subject that retains all the frequency components of the original signal and may still be less noisy and hence more useful to a user. Such a method of signal processing, for processing a periodic physiological signal of a subject, comprises the steps of a detecting step of detecting a cycle of the signal, an analysis step of determining a value of a characteristic of the cycle, a selection step of discarding or storing the cycle based on the determined value, and a concatenating step of concatenating the stored cycle signal for outputting for a user.

The method may have the advantage of making available to the user or a diagnostic device that uses such signals a signal that retains all the frequency components of the original signal but selected for being less noisy and hence more useful to the user than the original signal or a filtered signal.

A signal processing system for processing and conveying a periodic physiological signal to a user is also disclosed. The signal processing system comprises a probe for providing a periodic physiological signal, a detection unit for detecting a cycle of the signal, an analysis unit for determining a value of a characteristic of the cycle, a selection unit for discarding or storing the cycle based on the determined value, a concatenating unit for concatenating the stored cycle for generating a concatenated signal and an output unit for outputting the concatenated signal to a user.

Such a system may provide the advantage of conveying periodic physiological signals of a subject to a user that is more useful to the user than an unprocessed or a filtered signal.

BRIEF DESCRIPTION OF THE DRAWINGS

These and other aspects will be described in detail, by way of example, on the basis of the following embodiments and implementations, with reference to the accompanying drawings, wherein.

Corresponding reference numerals when used in the various figures represent corresponding elements in the figures.

DETAILED DESCRIPTION OF EMBODIMENTS

Figure 1:
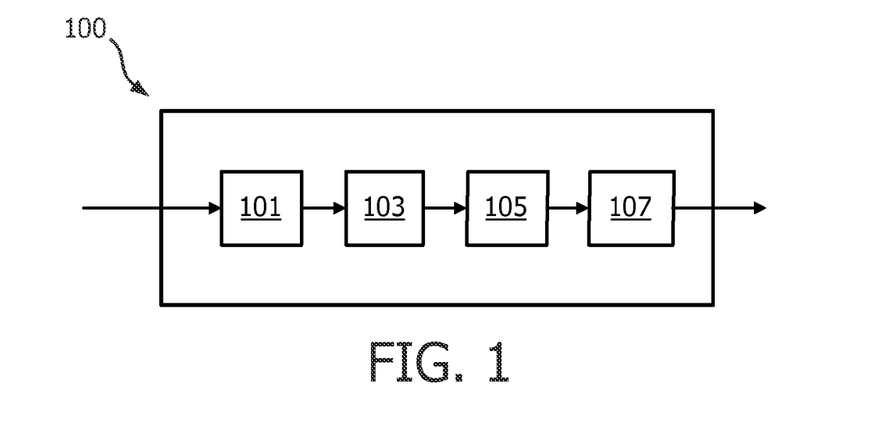
FIG. 1 is a schematic representation of an embodiment of the disclosed device.

The disclosed device, generally shown as 100 in FIG. 1, comprises a cycle detection unit 101 for detecting a single cycle of the periodic physiological signal. The analyzer unit 103 analyzes the detected cycle and determines a value of a characteristic of the cycle. A selection unit 105 either discards or stores the cycle based on the value of the characteristic using certain criteria. A concatenating unit (107) concatenates the stored cycle for generating a concatenated signal.

Examples of Periodic physiological signals could be a ECG signal, sounds of the heartbeats, sounds of the flow of blood due to the heart beats and sounds of respiration. Such a periodic physiological signal has noise signals along with the signal of interest. Filtering the noise signal may negatively impact at least a part of the spectrum of the original useful signal also. The disclosed device therefore, selects cycles of the signal that has low noise content.

The unit of the periodic signal considered is a cycle of the periodic signal. The cycle detection unit 101 detects a single cycle from the periodic signal for further analysis and processing. A single cycle may be detected based on the highest peaks of the signal, for instance. For instance, if the physiological signal is a heartbeat sound signal, the signal is sensed of a known length of time, digitized and stored. The peak values of the stored signal are detected. The time duration from one peak to the next may be compared to see if they are predominantly equal. If they are, the signal between any two consecutive peaks is deemed as one cycle.

The analysis unit 103 analyses the selected cycle of the signal and determines the value of a certain characteristic of the signal. For instance, the Signal to Noise Ratio (SNR) may be determined. For this purpose, all signal components above a certain frequency may be treated as noise. The inventors have found that, for example, by treating components of the signal with a frequency greater than 600 Hz and calculating the SNR is adequate for the purpose in case of a heart sound signal. However, 600 Hz is not the only frequency that could be used. Since the purpose of the SNR calculation is to obtain a figure of merit, any other frequency above which the heart sound does not have other significant frequency components could also be used. The selected frequency also depends on the frequency of the periodic physiological signal being handled and the frequency components it comprises.

The selection unit 105 stores a cycle if the value of the characteristic meets a certain predefined criteria. For instance, if the characteristic determined is the SNR, it selects the cycle for storing if the SNR is above a threshold.

The concatenating unit 107 concatenates the cycle selected and stored. It is to be understood here that if there is only one selected cycle, the concatenating unit repeatedly concatenates the cycle with the same cycle. In a practical implementation this may mean that the digitized cycle stored in a memory is repeatedly accessed or read and outputted so that it appears as consecutive cycles of a signal.

Figure 2:
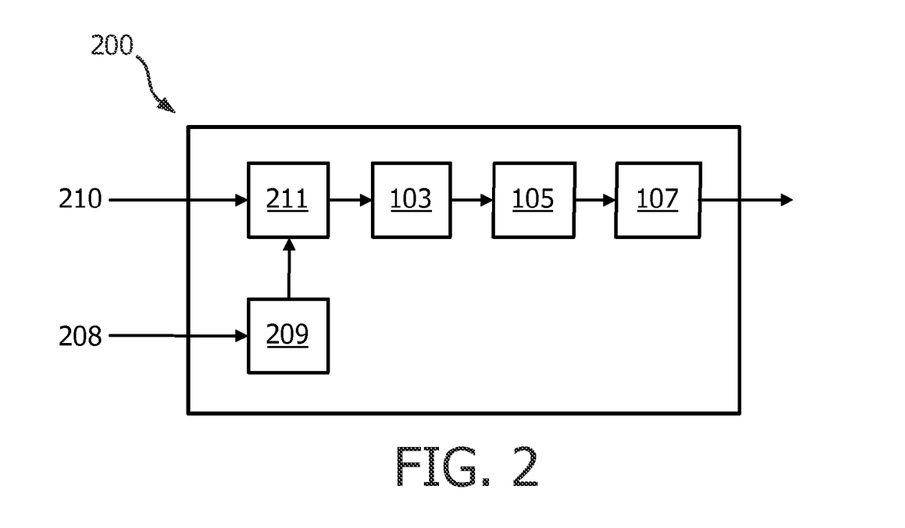
FIG. 2 is a schematic representation of another embodiment of the disclosed device.

In one embodiment, shown generally as 200 in FIG. 2, the device is configured to receive both the heart sound signal 210 and an ECG signal 208. The ECG signal has distinctive landmarks, generally referred to as P, QRS, T and U. This enables the determination of a single cycle of the ECG signal simple. Since the heartbeat sounds are synchronized with the ECG signal, it is easier to determine the single cycle of the heartbeat sound. In FIG. 2, the landmark detection unit 209 receives the ECG signal and detects the landmarks. Using the time instants of the detected landmarks the cycle detection unit 211 detects a single cycle of the heartbeat sound signal, for instance.

However, SNR is not the only characteristic that could be used for selecting or discarding a cycle of the signal. For instance, the heart sound has two distinct parts normally referred to as the S1 and S2 or the lub-dub sounds of the heart. The most useful cycles have a distinct S1 and S2 sounds. Thus a cycle may be selected for storage based on the energies of S1 and S2. Thus the characteristic the value of which is determined is the energy of S1 or S2 or preferably both. If the energy of S1 or S2 or the sum of S1 and S2 energies is above corresponding preset thresholds, such a cycle may be selected for storage, stored and concatenated. The inventors have found that the ratio of the sum of the energies of S1 and S2 and the total energy of the cycle is a suitable measure of the characteristic. In particular, if the energy ratio is greater than 0.5, it may be selected by the selection unit 105.

In one embodiment, the cycles are selected based on the values of more than one characteristic. In other words, the SNR and the ratio of the energies mentioned above are determined, for instance. If, for a given cycle, both the values are above the corresponding predetermined thresholds, the cycle is selected by the selection unit 105.

Figure 3:
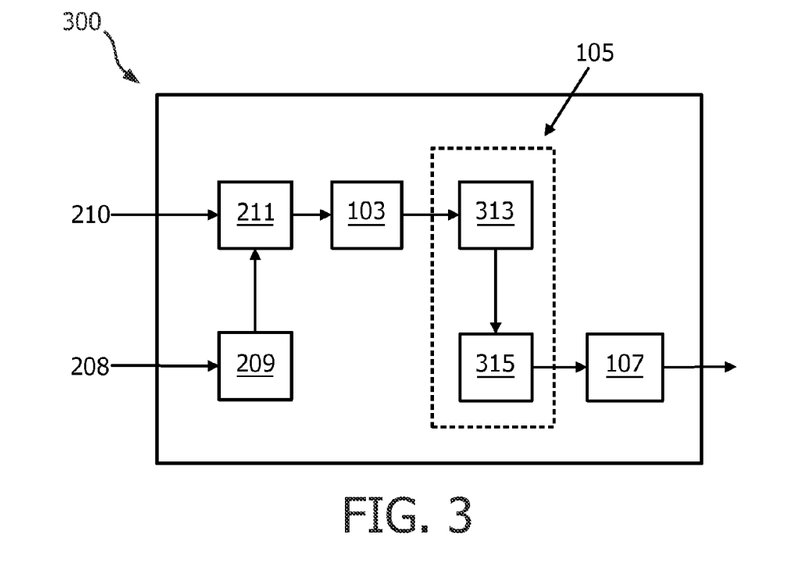
FIG. 3 is a schematic representation of another embodiment of the disclosed device.

In a further embodiment, shown generally as 300 in FIG. 3, has more than one selection unit. Initially, the selection unit 313 selects cycles based on the values of one or more characteristics. It continues doing this and stores a number of selected cycles in a second selection unit 315. The concatenating unit concatenates these cycles for outputting.

However, once the second selection unit has a predetermined number of cycles, they undergo selection once again on a different criterion. The cycles that do not meet the second criteria are discarded and the concatenation unit concatenates the remaining cycles.

The criterion used in the second selection unit may be based on the cycle time for instance. The rates of physiological signals vary with time. The heart rate falls when a person rests, for example, so that the heart rate is likely to be lower as the sounds are being processed since the subject is resting. The second selection may use this to further select cycles for concatenation. For example, the cycle times of all the stored cycles are calculated and their arithmetic mean is calculated by the second selection unit. Further, the standard deviation (SD or $\sigma$) of the cycle times is also calculated. Cycles having a cycle time greater than a threshold are selected and the others discarded. For example the criterion could be that only cycles with cycle times greater than the value obtained by subtracting the standard deviation from the mean are retained. Alternatively all cycles having cycle times within one standard deviation from the mean are selected. This has the advantage that the concatenated signal then consists of cycles with more uniform cycle times.

It must be noted here that the first selection unit 313 and the second selection unit 315 are described above as separate units for the sake of clearer understanding. However, in a practical device, the same selection unit may perform all the functions described. In such a case, the selection units 313 and 315 combined together may be referred to as 105 as before, as indicated with dotted lines in FIG. 3

Figure 4:
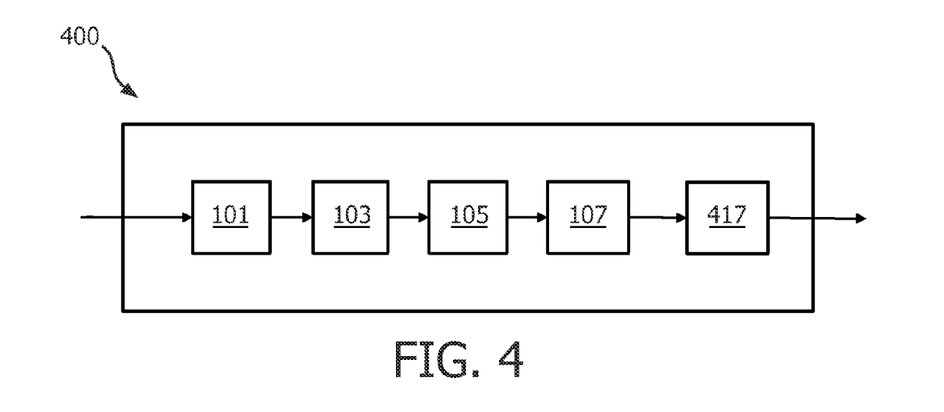
FIG. 4 is a schematic representation of another embodiment of the disclosed device.

FIG. 4 is a schematic diagram of another embodiment of the disclosed device which comprises an output unit 417 for outputting the concatenated signal in a form suitable for a user. The output unit could comprise one more drivers for driving an audio device—headphones for example, a video display unit, a tactile device, a digital storage unit and a printer. The user may, for instance, use one or more of these at the same time. For instance listening to the heart sounds while seeing the waveform of the heart sounds on the display unit (not shown). The user could also take a printout as a record for later use.

The device described hitherto could be used as an interface between a source of a periodic biological signal and devices that automatically identify pathological conditions of a subject's heart based on the heart sounds. For instance, the disclosed device could furnish the signal to a device such as the one described in the published patent specification WO-2009138932-A1, assigned to the same assignee as the present applicant. Since the signal is not filtered but still has a high SNR, the function of the device described in the cited specification is likely to be more robust than with an unprocessed or filtered signal.

A signal processing system is also described. Generally shown as 500 in FIG. 5, the system is for processing a periodic physiological signal and for conveying it to a user. Such a system comprises one or more sensors 519 for sensing the periodic physiological signal and generating a signal 210. The sensors may be of any suitable type from a group including but not limited to an electrets transducer, a electro-dynamic transducer, a piezoelectric transducer or a capacitive transducer. This may either be operatively connected permanently to the functional units in the enclosure or detachably connected to them. The system also comprises ECG electrodes and leads 521, such as those well known in the field, operatively connected either permanently to the functional units in the enclosure or detachably connected to them for providing the ECG signal. Single cycles of either the ECG signal or the other periodic physiological signals are detected in the cycle detection unit 211.

Figure 5:
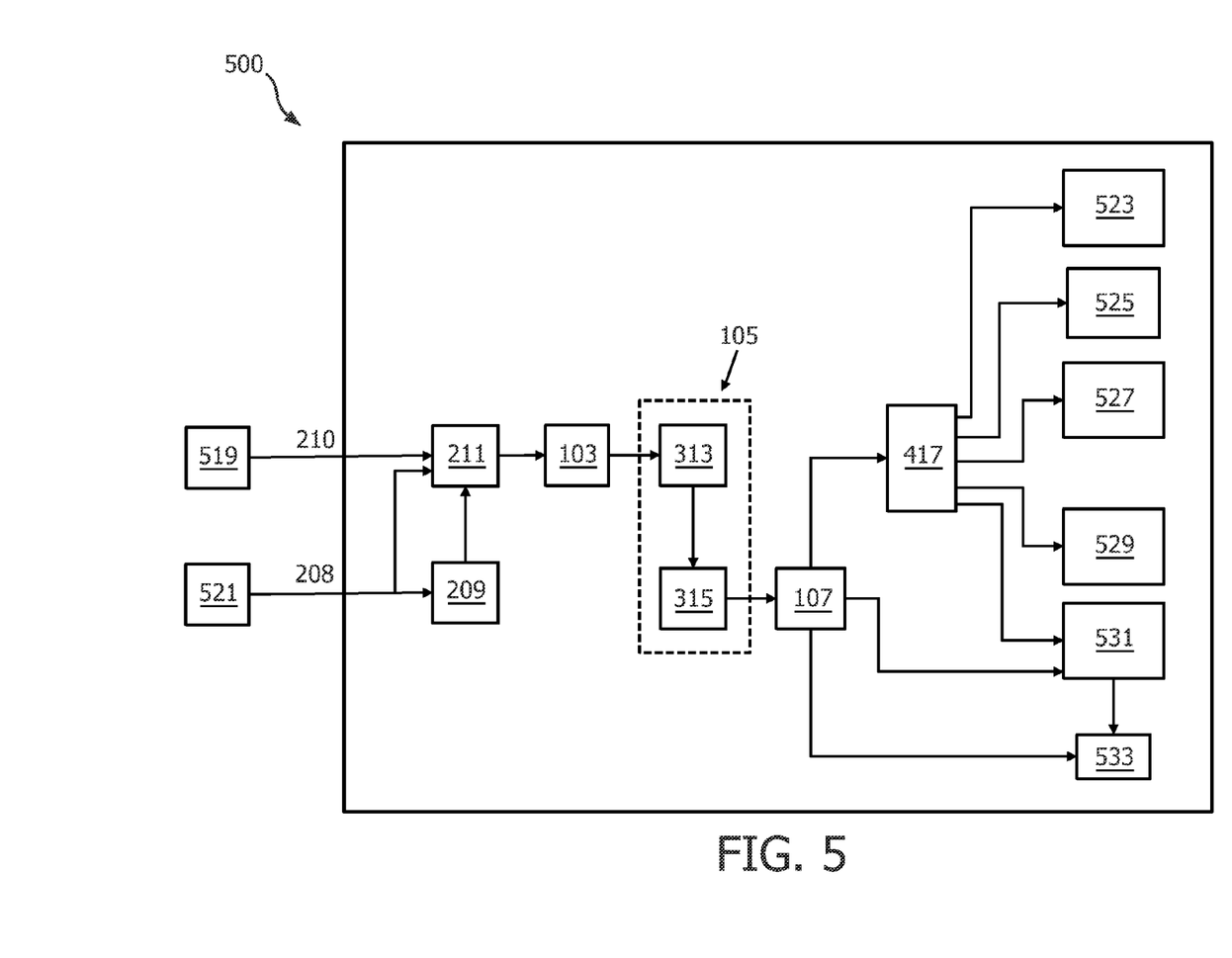
FIG. 5 is a schematic representation of an embodiment of the disclosed system.

As described earlier, cycles of the other periodic physiological signals may be detected with the aid of the ECG signals with the ECG landmark detection unit 209. The analysis unit 103 determines the value or values of the characteristics of the cycles detected by the cycle detection unit 103. The selection unit 313 selects signals for further operations based on the detected values of the chosen characteristic or characteristics. As described before, the second selection unit 315 may make a further selection based on other characteristics. The concatenation unit 107 concatenates the stored selected cycles. The concatenated signals are further processed by the output unit 417. The output signals are used to drive one or more of a visual display unit 523, an audio output transducer 525, a tactile unit 527, a printer 529 for printing the waveform and a storage unit 531 for storing the signal.

The storage device 531 may be a part of the system. It may also be a device for storing the concatenated signal on removable media such as an optical disc, for instance. The concatenated signal out of the concatenating unit 107 may be in digital form and may be stored as it is. Alternatively the output unit may compress the signal, preferably using lossless compression, for storing. These signals may also be output through an output connector 533, a USB connector for instance, for storage on other remote portable memory devices.

Even though the system is described as having elements from all the embodiments of the disclosed device, it need not necessarily be so. A designer of a system may choose a combination particularly suited for the type of signal that is to be processed and conveyed to the user, based on this disclosure. For instance, if only ECG signal is to be processed, the system need not have the audio related devices.

Figure 6:
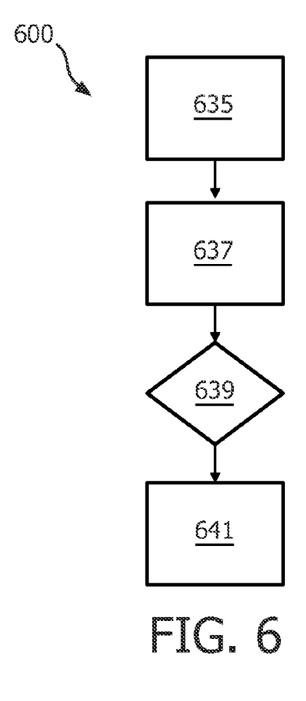
FIG. 6 is a representation of the disclosed method.

The disclosed method will now be described in detail with reference to FIG. 6. The disclosed method is shown generally as 600. In a detecting step 635, a single cycle of periodic physiological signals is detected.

One way of determining a cycle is to record the signal for a period long enough to record a known number of cycles. Since the range of frequencies of the periodic physiological signals being recorded is known it is possible to calculate the time needed for doing so. Then, the peaks of the signals are detected. The signal between two peaks is treated as one cycle.

Once a single cycle is detected, a known characteristic of the signal is determined in an analysis step 637. The most obvious characteristic is the Signal to Noise Ratio (SNR). The inventors have found that by treating components of the signal with a frequency greater than 600 Hz and calculating the SNR is adequate for heartbeat sound signals, as an exemplary periodic physiological signal. Similar threshold frequencies for other signals could be arrived at. However, even for the heartbeat sound signal 600 Hz is not the only frequency that could be used. Since the purpose of the SNR calculation is to obtain a figure of merit, any other frequency above which the periodic physiological signal does not have significant contribution could be used.

By using the equations given below, the SNR for the single cycle can be calculated. For instance, for the term $P_n(n)$, the upper cut off frequency of 4000 Hz is found to be a suitable frequency for a heartbeat sound signal as the energy of frequencies above this in the heart signal are negligible.

$$SNR_{global} = 10 \log \frac{\sum_{n=1}^{N} P_s(n)}{\sum_{n=1}^{N} Pn(n)},$$

where $$P_s(n) = \sum_{f=1}^{600} |X(f,n)|^2$$

and $$P_n(n) = \sum_{f=600}^{4000} |X(f,n)|^2$$

In a selection step 639 a cycle is discarded or selected for storing based on the value of the signal to noise ratio. Once at least one cycle is selected, it is concatenated in a concatenating step 641. Concatenating a single cycle is equivalent to replaying the same signal repeatedly.

As and when more cycles are selected for storing they are read out from the memory or replayed in a sequence repeatedly to provide a continuous concatenated signal.

Alternatively, the characteristic of the cycle of the periodic physiological signals that is determined in analysis step 637 is the energy of a certain part of the cycle. For instance, in the ECG signal, the energy of one of the waves in it could be determined. The parts could one or more of the P wave, the QRS wave, the T wave and the U wave.

For the heartbeat sound signal the calculation and the selection criteria may be expressed as below, wherein $S1_{energy}$, $S2_{energy}$ and $Sig_{energy}$ are the energies of the S1, S2 and the total signal respectively.

$$\frac{S1_{energy}(0-250 \text{ Hz}) + S2_{Energy}(0-250 \text{ Hz})}{Sig_{energy}(0-250 \text{ Hz})} > 0.5$$

Figure 7:
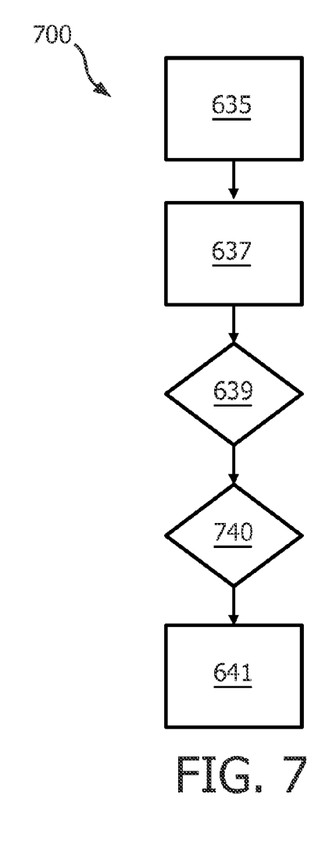
FIG. 7 is a representation of an implementation of the disclosed method

To have a signal that is more temporally uniform, in another implementation of the disclosed method, shown generally as 700 in FIG. 7, includes a second selection step 740. After the selection of individual cycles based on the values of one or more selected characteristics, in the second selection step 740, the time period of each cycle is measured and a further selection is made based on the time period of each cycle. One way of doing this is to calculate the mean and standard deviation of the cycle times of all the stored cycles and select only those cycles having a cycle time of at least one standard deviation subtracted from the mean. It may be expressed as an inequality as below wherein $T_{cycle}$ is the cycle time of a given cycle, $T_{mean}$ is the mean of the cycle times of all cycles selected previously based on one or more characteristic and σ is the standard deviation. With this, the variation between cycle times is limited and hence it is temporally more uniform than the concatenated signal of all the cycles initially selected, as described.

$$T_{cycle} > T_{mean} - \sigma$$

It is to be understood that the cycle time may be determined at the time of detecting a cycle in the cycle detection step. The cycle times may be used at the time of making the second selection.

While the embodiments have been described in detail in the drawings and description, such drawings and description are to be considered exemplary and not restrictive; the invention is not limited to the disclosed embodiments.

For example, it is possible to practice the invention in an arrangement wherein the hardware required for practicing the invention could be built as what is called an add-on unit or a retrofit unit and suitably interconnected to a conventional or prior art system or instrument. It is also possible that there are more than one computer memory units to store the cycle data and other data.

Other variations to the disclosed embodiments can be understood and effected by those skilled in the art, in practicing the claimed invention, from a study of the drawings, the disclosure, and the appended claims. In the claims, the word "comprising" does not exclude elements or steps other than those mentioned, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A signal processing device for processing a periodic physiological signal of a subject, the device comprising:
   a cycle detection unit for detecting a plurality of cycles of he periodic physiological signal;
   an analysis unit for determining a value including at least one of an energy characteristic of a selected part of a cycle and a ratio of the energy characteristic of the selected part of the cycle to the energy characteristic of the cycle;
   a selection unit for at least one of discarding or storing the cycle based on the determined value, wherein the selection unit stores the cycle based on the value of a first characteristic and subsequently discards the stored cycle when the stored cycle does not meet one or more criteria of a second characteristic that is different from the first characteristic; and
   a concatenating unit for outputting a concatenated signal that includes the stored cycles that are not discarded thereby outputting a modified periodic physiological signal that retain all the physiological frequency components of the stored cycles without including cycles that are discarded by the selection unit.

2. The device of claim 1, wherein the periodic physiological signal is representative of heartbeats of a subject.

3. The device of claim 2, comprising a sensor configured to receive an auditory signal and convert the auditory signal to the periodic physiological signal, wherein the periodic physiological signal is representative of a sound of the heartbeats of the subject.

4. The device of claim 3, wherein the cycle detection unit is configured for detecting the plurality of cycles based on peaks in the periodic physiological signal.

5. The device of claim 1, wherein the periodic physiological signal is an electrocardiogram signal, and wherein the cycle detection unit is configured for detecting the plurality of cycles from the electrocardiogram signal of a subject.

6. The device of claim 5, wherein the analysis unit is further configured for determining the time duration of the cycle based on the electrocardiogram signal.

7. The device of claim 1, wherein the analysis unit is configured for determining at least one of a Signal to Noise Ratio and a time duration of the cycle.

8. The device of claim 1, wherein the selection unit is configured for storing the cycle when the cycle has the determined value meeting one or more criteria.

9. The device of claim 8, wherein the one or more criteria of the second characteristic is based on statistical quantities associated with the stored cycles that are not discarded.

10. The device of claim 1, further comprising an output unit for outputting the concatenated signal to at least one of an electro-acoustic audio transducer, a visual display, a memory device for storing as a digital audio signal, and a printer in a print format.

11. The device of claim 1, comprising a sensor configured to receive an auditory signal and convert the auditory signal to the periodic physiological signal, wherein the periodic physiological signal is representative of a sound of heartbeats and the analysis unit is configured to determine the value of at least one of the energy characteristic of at least one of S1 sound and S2 sound of the cycle, and a ratio of the energy characteristic of at least one of the S1 sound and the S2 sound of the cycle to the energy characteristic of the cycle.

12. The device of claim 11, the selection unit being configured to utilize a length of time of the cycle as the second characteristic.

13. The device of claim 12, the selection unit being configured to calculate a standard deviation and a mean of the length of time of only the stored cycles that are not discarded for determining the second characteristic.

14. The device of claim 1, the selection unit being configured to utilize a length of time of the cycle as the second characteristic.

15. The device of claim 14, the selection unit being configured to calculate a standard deviation and a mean of the length of time of only the stored cycles that are not discarded for determining the second characteristic.

16. A signal processing system for processing a periodic physiological signal and for conveying it to a user, the system comprising:
   a probe configured to receive an auditory signal and provide the periodic physiological signal in response to the received auditory signal,
   a detection unit for detecting a cycle of the periodic physiological signal provided by the probe;
   an analysis unit for determining a value including at least one of an energy characteristic of a selected part of the cycle and a ratio of the energy characteristic of the selected part of the cycle to the energy characteristic of the cycle;
   a selection unit for at least one of discarding or storing the cycle based on the determined value, wherein the selection unit stores the cycle based on the value of a first characteristic and subsequently discards the stored cycle when the cycle does not meet one or more criteria of a second characteristic that is different from the first characteristic;
   a concatenating unit for generating a concatenated signal that includes the stored cycle that is not discarded; and
   an output unit for outputting the concatenated signal to a user thereby outputting a modified periodic physiological signal that retains all the physiological frequency components of the stored cycle without including cycles that are discarded by the selection unit.

17. The system of claim 16, wherein the output unit is configured to output the signal through one or more output devices from a group comprising an audio output device, a video display, a tactile output device and a printer.

18. A method of signal processing for processing a periodic physiological signal, the method comprising acts of:
  detecting a plurality of cycles of the signal;
  determining a value including at least one of an energy characteristic of a selected part of a cycle and a ratio of the energy characteristic of the selected part of the cycle to the energy characteristic of the cycle;
  at least one of discarding or storing the cycle based on the determined value, wherein the cycle is stored based on the value of a first characteristic and the stored cycle is subsequently discarded when the stored cycle does not meet one or more criteria of a second characteristic that is different from the first characteristic;
  outputting a concatenated signal that includes the stored cycles that are not discarded thereby outputting a modified periodic physiological signal that retains all the physiological frequency components of the stored cycles without including cycles that are discarded by the selection unit.

19. The method of claim 18, wherein the periodic signal is representative of heartbeats of a subject.

\* \* \* \* \*